United States Patent [19]

Rosencwaig et al.

[11] Patent Number: 4,634,290
[45] Date of Patent: * Jan. 6, 1987

[54] METHOD AND APPARATUS FOR DETECTING THERMAL WAVES

[75] Inventors: Allan Rosencwaig, Danville; Jon Opsal, Livermore, both of Calif.

[73] Assignee: Therma-Wave, Inc., Fremont, Calif.

[ * ] Notice: The portion of the term of this patent subsequent to Apr. 1, 2003 has been disclaimed.

[21] Appl. No.: 797,949

[22] Filed: Nov. 14, 1985

Related U.S. Application Data

[62] Division of Ser. No. 612,075, May 21, 1984, Pat. No. 4,579,463.

[51] Int. Cl.$^4$ ...................... G01N 21/41; G01N 25/00
[52] U.S. Cl. ........................................ 374/5; 356/432; 374/57; 374/121
[58] Field of Search .................... 374/121, 45, 55, 117, 374/57, 5, 6, 7; 356/432, 357, 351

[56] References Cited

U.S. PATENT DOCUMENTS 4,243,327  1/1981  Frosch et al. ................... 356/432
4,358,201  11/1982  Makosch ........................ 356/351

*Primary Examiner*—Daniel M. Yasich
*Attorney, Agent, or Firm*—Limbach, Limbach & Sutton

[57] ABSTRACT

A method and apparatus is disclosed for detecting thermal waves. This system is based on the measurement of the change in reflectivity at the sample surface which is a function of the changing surface temperature. The apparatus includes a radiation probe beam that is directed on a portion of the area which is being periodically heated. A photodetector is aligned to sense the intensity changes in the reflected radiation probe beam which results from the periodic heating. These signals are processed to detect the presence of thermal waves.

8 Claims, 3 Drawing Figures

METHOD AND APPARATUS FOR DETECTING THERMAL WAVES

This is a division of application Ser. No. 612,075 filed May 21, 1985, now U.S. Pat. No. 4,579,463.

TECHNICAL FIELD

The subject invention relates to a new and improved method and apparatus for detecting thermal waves generated in a sample. More particularly, a noncontact measurement technique is disclosed wherein the periodic temperature induced change in reflectivity of a sample surface is monitored by testing the intensity variations of an electromagnetic probe beam that is reflected off the sample surface. The intensity variations of the probe beam are used to detect thermal waves in a sample.

BACKGROUND OF THE INVENTION

There is presently a significant amount of research being conducted in the field of thermal wave microscopy. In thermal wave microscopy, a periodic heat source is focused on the surface of a sample. The heat source is typically supplied by either an intensity modulated laser beam or a stream of particles, such as an electron beam. When the sample absorbs the incident energy at or near the sample surface, a periodic surface heating results which, in turn, generates thermal waves that propagate from the irradiated spot. These thermal waves have the same frequency as the beam modulation frequency. The wavelength of the thermal waves is determined both by the frequency of the beam and by the thermal parameters of the sample.

In a thermal wave microscope, thermal features beneath the sample surface are detected and imaged by sensing the thermal waves that scatter and reflect from these features. The thermal waves are highly damped such that they travel only one or two wavelengths before becoming too weak to detect. Nevertheless, a variety of methods have been developed capable of sensing and measuring the thermal waves generated in the sample.

One method of detection includes the sensing of acoustic waves which are generated by the thermal waves. More particularly, acoustic waves are generated because the thermal waves induce stress-strain oscillations in the heated region of the sample. These elastic waves are true propagating waves and can be detected with conventional ultrasonic transducers. This technique disclosed in U.S. Pat. No. 4,255,971, issued Mar. 17, 1981, assigned to the same assignee as the subject invention, and which is incorporated herein by reference.

As can be appreciated, the above described system, utilizing a piezoelectric crystal, is a "contact" technique requiring the attachment of the transducer to the sample. The latter requirement is time-consuming and potentially contaminating and is not suitable for production situations encountered in the semiconductor industry. Accordingly, there has been significant work carried out in developing noncontact detection techniques. One such noncontact detection technique is described in copending applications, Ser. No. 401,511, filed July 26, 1982, and now U.S. Pat. No. 4,521,118, issued June 4, 1985, and Ser. No. 481,275, filed Apr. 1, 1983 and now U.S. Pat. No. 4,522,510, issued June 11, 1985, both incorporated by reference.

The latter applications describe a method and apparatus for detecting thermal waves by monitoring the local angular changes occurring at the surface of the sample. More specifically, when thermal waves are generated in a localized region of the sample, the surface of the sample undergoes periodic angular changes within the periodically heated area because of local thermoelastic effects. These angular changes occur at a frequency equal to the frequency of the modulated heating beam. To monitor these changes, a beam of energy, such as a laser beam, is focused on the surface of the sample in a manner such that is reflected. Because of the local angular changes occurring at the surface of the sample, the reflected beam will experience angular displacements in a periodic fashion. By measuring the angular displacements, information about the thermal wave activity in the sample can be determined. The latter technique has proved to be a highly sensitive process for detecting thermal waves.

The subject invention, in contrast, is directed towards an independent and totally different method of detecting thermal waves. The technique disclosed herein may be used as an independent basis for the detection of thermal waves. In addition, when used in combination with any of the earlier described techniques, new and surprising additional information may be obtained about the characteristics of a sample. The advantages of using two different thermal wave detection techniques to gain additional information about a sample is described in detail in copending application, Ser. No. 612,077, filed May 21, 1984, assigned to the same assignee as the subject invention and incorporated herein by reference. These advantages are discussed briefly below.

In the above described techniques, such as monitoring the deflection of a probe beam or through detection of acoustic waves through a transducer, the output signals generated are primarily a function of the integral of the temperature distribution through the sample. In contrast, in the subject system, which is based on measurements of reflectivity, the output signals are primarily a function of surface temperature. The availability of two independent measurements of thermal wave signals permits the evaluation of both thickness and compositional variables in a sample. The latter concepts are set forth in detail, and are the subject of the copending application cited above, which is incorporated herein by reference. It should be understood, however, that the subject invention not only provides a new detection technique, but in addition, when combined with other measurement techniques, defines a completely new and powerful analytical tool with capabilities not found in the prior art.

Accordingly, it is an object of the subject invention to provide a new and improved apparatus and method for detecting thermal waves.

It is another object of the subject invention to provide a new and improved apparatus and method which detects thermal waves based on changes in reflectivity of the sample.

It is still a further object of the subject invention to provide a new and improved method and apparatus for detecting thermal waves which is based on surface temperature variations.

SUMMARY OF THE INVENTION

In accordance with these and many other objects, the subject invention provides for a new and improved method and apparatus for detecting thermal waves. The method and apparatus is based on the principle that the changes in optical reflectivity of a sample, occurring as it is periodically heated, will vary, depending on the thermal characteristics of the sample. It has been known that optical reflectivity is dependent, to some extent, on temperature. This dependence is defined by the following equation:

$$R_T = R_o + (\partial R/\partial T)(\Delta T) \qquad (1)$$

In this equation, $R_o$ represents the reflectivity at a set temperature and the second term in the equation gives the change of reflectivity resulting from the change in surface temperature. The term $(\partial R/\partial T)$ is the temperature coefficient of reflectivity which represents the rate of change in reflectivity with respect to the change in temperature. The term $\Delta T$ is the changing temperature at the sample surface.

The first term $R_o$ is at least four orders of magnitude greater than the second term for temperature changes, $\Delta T$ of less than 100°. Furthermore, the noise level associated with $R_o$ as measured with a photodetector, is on the order of $\sqrt{R_o}$. The latter value is still 100 times greater than the second term of the equation which makes measurement of the second term quite difficult. In absolute terms, the value of the ratio $(\partial R/\partial T)(\Delta T)/R_o$ is on the order of $10^{-4}$ to $10^{-5}$ and, therefore, has not been used as a measurement parameter.

In accordance with the subject invention, this difficulty is overcome by modulating the heating source. Periodic changes in reflectivity which are occurring at the frequency of the modulation beam are then monitored. This information is processed by passing the signal through narrow bandwidth filters. The result is that only the periodic reflectivity signal $\Delta R_T$, as a result of the periodic temperature variations $\Delta T$, is measured, rather than absolute reflectivity $R_T$.

The periodic reflectivity signal $\Delta R_T$ is defined by the following equation:

$$\Delta R_T = (\partial R/\partial T)(\Delta T) \qquad (2)$$

As seen from the above equation, the periodic reflectivity signal $\Delta R_T$ is dependent on the temperature coefficient of reflectivity $(\partial R/\partial T)$ times the periodic surface temperature $(\Delta T)$. The periodic reflectivity signal $\Delta R_T$ thus provides a measure of the periodic surface temperature $\Delta T$. The periodic surface temperature, in turn, provides information about thermal wave propagation and interaction in the material. Thus, with suitable mathematical equations, one can determine the thermal wave activity based on the measured changes in reflectivity. Calculation of the thermal waves is carried out by normalizing the signals against a known reference sample, as discussed in greater detail below.

Based on the foregoing principles, a method and apparatus is disclosed for detecting the presence of thermal waves. As set forth above, thermal waves are created by generating a periodic localized heating at a spot on the surface of a sample. In accordance with the subject invention, the apparatus for detecting the thermal waves includes a radiation probe beam which is directed on a portion of the periodically heated area on the sample surface in a manner such that the radiation probe beam reflects off that surface. A means is provided for measuring the intensity variations of the reflected radiation probe resulting from the periodic heating. Finally, a means is provided for processing the measured intensity variations from the reflected radiation probe to detect the presence of thermal waves.

Further objects and advantages of the subject invention will become apparent from the following detailed description taken in conjunction with the drawings in which:

BEST MODE FOR CARRYING OUT THE INVENTION

Figure 1:
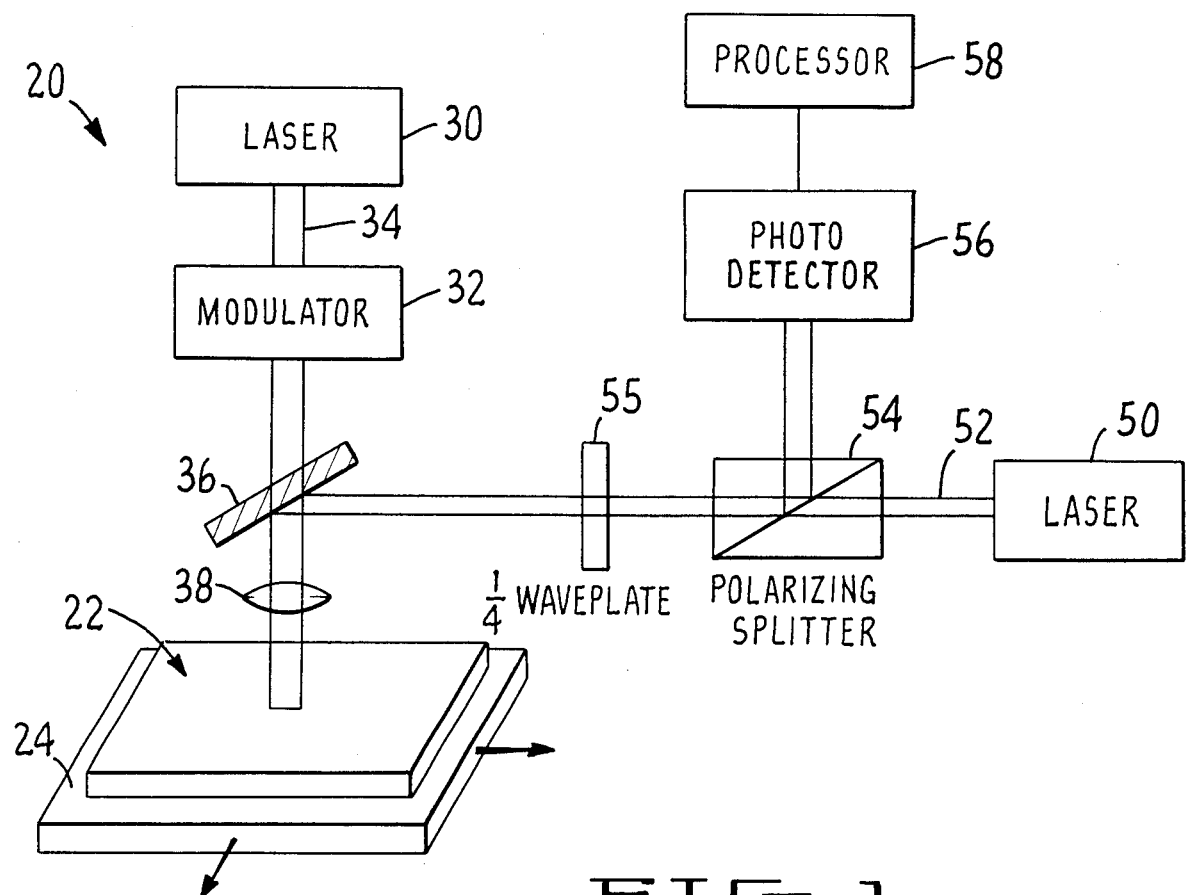
FIG. 1 is a composite block and schematic diagram of the apparatus for carrying out the detection of thermal waves in accordance with the subject invention.

Referring to FIG. 1, there is illustrated the apparatus 20 for carrying out the method of the subject invention. A sample 22 is shown resting on a platform 24. Platform 24 is capable of movement in two orthogonal directions in a manner such that the sample can be rastered with respect to the heating and probe beams of the subject invention. Controllable stages are well known in the art and also disclosed in U.S. Pat. No. 4,255,971, cited above.

As illustrated in FIG. 1, a means is shown for generating thermal waves. This means is defined by laser 30 which is intensity modulated by modulator 32. In the preferred embodiment, beam 34 is focused on the surface of the sample by a microscopic objective 38. Beam 34 is intended to create a periodic surface heating at the sample surface. This periodic heating is the source of thermal waves that propagate outwardly from the center of the beam. The thermal waves interact with thermal boundaries and barriers in a manner that is mathematically equivalent to scattering and reflection of conventional propagating waves. Any features on or beneath the surface of the sample that have thermal characteristics different from their surroundings will reflect and scatter thermal waves and thus become visible to these thermal waves.

The intensity modulated heating source could be supplied by electromagnetic radiation at various wavelengths, including X-rays, gamma rays, infrared, ultraviolet, visible light, microwaves or radio frequencies. The intensity modulated source can also be generated through thermal excitations arising from the interaction of the sample with an intensity modulated stream of particles, such as a beam of electrons, protons, neutrons, ions or molecules. However, because of the ease of directing and focusing a laser beam, it is believed that the illustrated embodiment is preferable.

The intensity modulated beam 34 is passed through dichroic mirror 36 prior to passing through the microscopic objective 38. In the preferred embodiment, the heating beam is an argon ion laser and the dichroic mirror is transparent to argon ion radiation. As will be discussed below, the dichroic mirror functions to reflect the measuring laser beam, which is preferably generated by a helium-neon laser.

In accordance with the subject invention, a new and improved method and apparatus is provided for detecting the thermal waves which are being generated in the sample. The detection system includes a light probe for emitting a beam 52 which is directed on the surface of the sample that has been periodically heated by the modulated energy beam 34. In the illustrated embodiment, the light probe beam 52 is generated by helium-neon laser 50. Various other sources of electromagnetic radiation may be used for the probe beam as long as the beam reflectivity is affected by the temperature changes on the sample surface in a manner which can be measured.

Probe beam 52, emanating from the helium-neon laser 50, is then passed through a polarizing splitter 54. The polarizing splitter is oriented in a manner such as to let the coherent light emanating from laser 50 to pass freely therethrough. The splitter will, however, deflect all light whose phase has been rotated through 90° relative to beam 52. The reason for this arrangement will become apparent below.

Light probe beam 52 is then passed through a $\frac{1}{8}\lambda$-waveplate 55. Waveplate 55 functions to rotate the phase of the probe beam by 45°. As can be appreciated, on the return path of the beam, the waveplate will rotate the phase of the beam another 45° so that when it reaches splitter 54 the phase of the beam will have been rotated a total of 90° from the incoming orientation. By this arrangement, the splitter 54 will deflect the retro-flected light beam up to detector 56, as discussed in more detail below.

After the probe beam 52 initially passes through waveplate 55, it is reflected downwardly by dichroic mirror 36. As pointed out above, the dichroic mirror is transparent to argon ion light but will reflect the light rays in the helium-neon frequencies. In the preferred embodiment, the heating beam and the probe beam are aligned in such a manner that they are directed in a coincident manner down through lens 38 and focused at the same spot on the surface of the sample. By focusing the probe beam and the heating beam at the same spot, the maximum signal output can be achieved.

It is to be understood that the reflectivity signals of interest exist at any areas on the surface of the sample which has been periodically heated by the beam 34. Therefore, the probe beam does not have to be directly coincident with the heating beam 34 to detect the signals of interest. Accordingly, a microscope objective is not necessary for focusing either the heating beam 34 or the probe beam 52. Rather, it is only necessary to direct the probe beam within at least a portion of the area periodically heated by beam 34. A discussion and equations for calculating the size of the periodically heated area are set forth in U.S. Pat. No. 4,521,118, cited above. Briefly, the diameter of the heated area, which extends radially away from the center of the heating beam, is a function of the modulation frequency and the diameter of the heating beam and of the thermal parameters of the sample.

Because the signals to be measured are so small, on the order of $10^{-5}$ of the DC level of the probe beam, every effort should be made to maximize the output for detection. Accordingly, it is desirable to direct the probe beam essentially coincident with the heating beam. Direction of the probe beam can be accomplished by movement of mirror 36. The alignment of the probe beam with the heating beam should be contrasted with the measuring technique described in U.S. Pat. No. 4,521,118, cited above, wherein the probe beam is preferably directed off center from the heating beam but within the periodically heated area. As set forth in detail in the latter specification, the probe beam is intended to measure angular changes in the surface of the sample. However, the surface of the sample at the center of the heating beam undergoes only vertical movements. The angular surface changes occur in areas on the surface spaced from the center of the heating beam.

Figure 2:
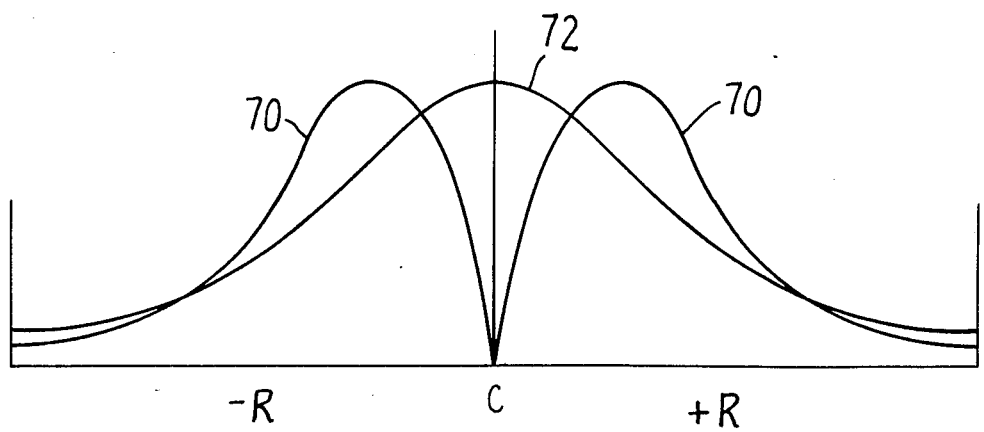
FIG. 2 is a graphical representation comparing the available signal strength in both reflectivity and deflection-type thermal wave detection systems, measured as a function of the distance on the sample surface from the heating source.

A graphical representation of the signal strength available for detection by these two techniques, as a function of the distance on the sample surface from the heating source, is illustrated in FIG. 2. In that figure, the horizontal axis indicates the distance away from that central heating point C on the surface of the sample. The vertical axis is a measure of available signal strength. Curve 70 represents signals available in the deflection detection technique, while curve 72 illustrates signal strength available with the subject reflectivity detection technique. As will be seen from curve 70, the maximum output signals measurable in the deflection technique are at a minimum adjacent the center of the heating beam. The signals increase at positions located radially outwardly from the center and then taper off towards the border of the periodically heated area. The actual dimensions of the periodically heated area can be calculated by the equations set forth in the prior application. In contrast, curve 72 indicates that the reflectivity output signal is maximized when the probe beam is centered on the heating beam. From FIG. 2 it should be apparent that in the subject technique, maximum signal output can be achieved by focusing the probe beam to be coincident with the heating laser beam.

As the probe beam is reflected off the surface of the sample, it interacts with the electrons and thus with the lattice structure of the sample at its surface. The lattice structure of the sample will undergo periodic changes as the temperature of the sample changes periodically. The probe beam essentially "sees" the changes of this lattice structure and the level of the intensity of the beam changes along with the changing thermal conditions of the sample surface.

The probe beam is then reflected back up to the dichroic mirror where it is, in turn, reflected back along the incoming path and through the $\frac{1}{8}\lambda$-waveplate 55. As discussed above, waveplate 55 rotates the phase of the probe beam by another 45° such that when the beam reaches splitter 54, its phase has been rotated 90° with respect to the original beam. Accordingly, this splitter will deflect the retro-reflected probe beam upwardly towards detector 56.

Since intensity variations of a radiation beam are to be detected, a standard photodetector may be employed as a sensing mechanism. The intensity variations which are measured are then supplied as an output signal to a processor for deriving the data on the thermal waves based on the changing surface temperature conditions as indicated by the changing output signal.

Figure 3:
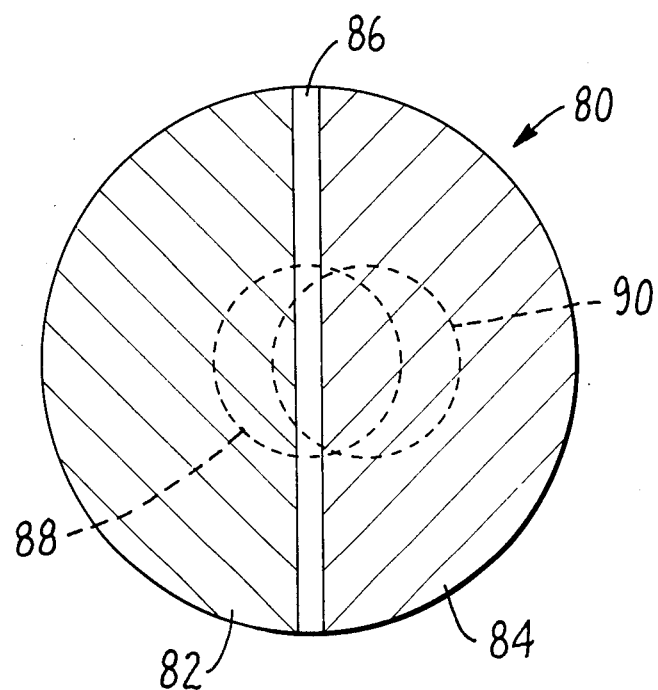
FIG. 3 is a bottom plan view of a typical split cell photodetector which may be utilized in the subject invention.

(1) FIG. 3 illustrates one type of photodetector 80 which is suitable for performing the intensity measurements of the subject invention. Photodetector 80 is referred to as a split cell detector and can be used not only to measure variations in intensity of the probe beam (as shown in phantom line at 88) due to changes in periodic reflectivity of the sample, but can also be used to measure changes in the angular displacement of the probe beam. Thermal wave measurement by detection of the angular changes in a probe beam is described in U.S. Pat. Nos. 4,521,118, and 4,522,510, cited above.

(2) Split cell detector 80 is defined by a photodetector having two sensing elements 82 and 84 located in a side-by-side arrangement separated by a divider 86 only a few microns thick. Each element 82, 84 generates an electrical signal proportional to the number of photons reaching that sector. Where the split cell is to be used to measure angular deviations of the probe beam, processor 58 functions to subtract the output of one sector from the output of the other. If, on the other hand, changes in reflectivity of the sample are to be measured, the output of elements 82 and 84 is summed.

(3) The sum of the signals of both segments gives a measure of the absolute value of the light energy falling on the photodetector. As the total number of photons reflected from the sample surface changes in response to the changes in optical reflectivity of the sample, the summed output signal of the photodetector will change in proportion. This result is true even it the beam is experiencing angular displacements due to the angular changes on the surface of the sample, as depicted in FIG. 3. Stated differently, even if the beam (shown in phantom line at 90) is located off center of the photocell, the sum of the two sides will still give a value of the total amount of energy reaching the surface of the photodetector. Thus, when the processor adds the output signals from the photodetector, the result will be independent of changes in the position of the probe bream.

(4) By analogy, the output of detector 80 (when measuring changes in reflectivity of the sample), will also be unaffected by the small changes in the diameter of the probe beam which may be induced by the periodic heating. As described in applicants' prior U.S. Pat. No. 4,522,510, periodic heating of a sample can create a periodically changing thermal lens in the sample. The presence of the thermal lens can be monitored by using a probe beam. For example, if a probe beam is passed, off-axis, through a periodically changing thermal lens, the beam will be periodically deflected. If the probe beam is passed through the center of thermal lens, its diameter will vary periodically by a small amount. The latter effect is described in U.S. Pat. No. 4,243,327 issued Jan. 6, 1981, to Frosch.

(5) The patent to Frosch describes a method for detecting the changes in diameter of a reflected probe beam induced by a changing thermal lens. This method is based on the principle that as the probe beam varies in diameter, the number of photons striking a fixed area having a diameter that is smaller than the probe beam diameter, will vary over time. Thus, the detector in Frosch is designed to measure the number of photons striking a particular area over time, that is, the areal density of the photons at the detector surface.

(6) In contrast, and as discussed above, in the subject device, the detector 56(80), in combination with processor 58, is arranged to measure the total amount of photons reflected from the sample, without regard to the location at which the photons impact on the detector or the areal density of those photons at the detector surface. In fact, since the output of detector 56 is proportional to the number of photons reflected from the sample surface, the resulting signals will be *unaffected* by the small changes in the beam diameter which may be induced by the periodic heating. Thus, in the subject device, the measurement of intensity changes of the reflected probe beam due to changes in reflectivity of the sample is independent of relatively small changes in both the position of the beam on the detector, as well as the diameter of the beam.

(7) As pointed out above, detector 56 is arranged so that the total amount of power in the reflected probe beam is measured. This measurement could not be accomplished if any portion of the probe beam moved off the surface of the detector. As can be appreciated, if part of the probe beam misses the detector surface, the output signals therefrom would not be proportional to the total number of photons in the reflected probe beam. Therefore, it is necessary that the apparatus be arranged such that the diameter of the probe beam underfills, or is less than, the active surface of the photodetector (i.e. falls within its boundary), as shown in FIG. 3.

The operation of processor 58 is dependent on the type of testing configuration which is utilized. In all cases, the processor is designed to evaluate the intensity changes of the incoming probe beam which are the result of the periodic reflectivity changes caused by the periodic heating on the sample. These periodic intensity changes are filtered to produce a signal which may be evaluated.

The derivation of thermal wave signals from the periodic reflectivity signal is carried out by normalizing either the phase or magnitude of the measured signal. These normalized values are then compared to normalized values taken from a known reference sample. Calculations of this general type are discussed in "Thermal Wave Depth Profiling: Theory" by Jon Opsal and Allan Rosencwaig, *Journal of Applied Physics,* June, 1982. The calculations set forth in the latter article are based on detection techniques which measure an output signal that is a function of the integral of the temperature beneath the sample surface. As discussed above, the subject detection system measures an output signal which is primarily a function of the surface temperature and therefore the calculations must be modified accordingly.

Once the thermal wave information is derived, an analysis can be performed to provide significant information about a sample. Various types of thermal wave analysis are set forth in copending application, Ser. No. 389,623, filed June 18, 1982, and now U.S. Pat. No. 4,513,384, issued Apr. 23, 1985, incorporated herein by reference. For example, an evaluation can be made of the thickness of thin film layers. In addition depth profiling varying thermal parameters is possible.

Referring again to FIG. 1, a controllable stage 24 is provided to simplify the movement of the sample with respect to the heating and probe beams. By this arrangement, a two-dimensional thermal wave image may be readily generated. In the alternative, in a manufacturing setting, point testing may be utilized to evaluate if a particular fabrication step has been successful. Thermal wave analysis is particularly suited for the evaluation of integrated circuits.

In summary, there has been disclosed a new and improved method and apparatus for detecting thermal waves which have been generated in a sample by a periodic localized heating at a spot on the sample surface. The subject invention includes a radiation probe beam which is directed onto a portion of the area which has been periodically heated, in a manner such that it reflects off the surface of the sample. A means is provided for measuring the intensity variations of the reflected radiation probe beam resulting from the periodic heating. A processing means is provided for analyzing the intensity variations of the reflected radiation probe beam to detect the presence of thermal waves.

While the subject invention has been described with reference to a preferred embodiment, various other changes and modifications could be made therein, by one skilled in the art, without varying from the scope and spirit of the subject invention as defined by the appended claims.

We claim:

1. An apparatus for detecting thermal waves in a sample, by measuring intensity variations of a reflected probe beam resulting from periodic changes in optical reflectivity of the sample induced by the thermal waves, said thermal waves being generated by a periodic localized heating at a spot on the surface of the sample, said apparatus comprising:

a probe beam for emitting a beam of radiation;
   means for directing the radiation probe beam within a portion of the periodically heated area on the sample surface in a manner such that the radiation probe beam reflects off the surface of the sample;
   means for measuring the intensity variations of the reflected radiation probe beam resulting from the periodic changes in optical reflectivity of the sample induced by the periodic heating with the measured intensity changes being independent of changes in diameter or position of the probe beam; and
   means for processing the measured intensity variations of the reflected radiation probe to detect the presence of the thermal waves.

2. An apparatus as recited in claim 1 wherein said means for directing said radiation probe beam is arranged to direct said probe beam at the center of the area which has been periodically heated.

3. An apparatus as recited in claim 1 wherein said means for measuring the intensity variations of the reflected radiation probe beam is a photodetector.

4. An apparatus as recited in claim 3 wherein said probe beam is directed to underfill the surface of the photodetector.

5. An apparatus as recited in claim 1 wherein said radiation probe is defined by a laser.

6. An apparatus as recited in claim 1 further including a means for rastering the sample with respect to the radiation probe beam.

7. A method of detecting thermal waves in a sample by measuring intensity variations of a reflected probe beam resulting from periodic changes in optical reflectivity of the sample induced by the thermal waves, said thermal waves being generated by a periodic localized heating at a spot on the surface of the sample, said method comprising the steps of:

directing a radiation probe beam within a portion of the periodically heated area on the surface of the sample in a manner such that the radiation beam reflects off the surface of the sample;
   measuring the intensity variations of the reflected radiation beam resulting from the periodic changes in optical reflectivity of the sample induced by said periodic heating with the measured intensity changes being independent of changes in diameter or position of the radiation beam, and
   processing the measured intensity variations of the reflected radiation beam to detect the presence of thermal waves.

8. A method as recited in claim 6 wherein said radiation beam is directed at the center of the area periodically heated by said periodic localized heating.

* * * * *